United States Patent [19]

Iwanczyk et al.

[11] Patent Number: 5,773,829
[45] Date of Patent: Jun. 30, 1998

[54] RADIATION IMAGING DETECTOR

[76] Inventors: Jan S. Iwanczyk, 3066 Corda Dr., Los Angeles, Calif. 90049; Bradley E. Patt, 5416 Katherine Ave., Sherman Oaks, Calif. 91401

[21] Appl. No.: 743,320

[22] Filed: Nov. 5, 1996

[51] Int. Cl.⁶ .................................................. G01T 1/20
[52] U.S. Cl. ................... 250/367; 250/368; 250/370.09; 250/370.11; 250/370.15
[58] Field of Search ................................ 250/366, 367, 250/368, 370.09, 370.11, 370.15, 369, 363.1

[56] References Cited

U.S. PATENT DOCUMENTS

| | | | |
|---|---|---|---|
| 2,853,621 | 9/1958 | Ruderman | 250/370.11 |
| 4,672,207 | 6/1987 | Derenzo | 250/370.11 X |
| 4,982,096 | 1/1991 | Fujii et al. | 250/370.11 X |
| 5,132,542 | 7/1992 | Bassalleck et al. | 250/370.09 |
| 5,144,141 | 9/1992 | Rougedt et al. | 250/370.11 X |
| 5,235,191 | 8/1993 | Miller | 250/370.11 X |
| 5,245,191 | 9/1993 | Barber et al. | 250/370.09 X |
| 5,532,475 | 7/1996 | Tonami et al. | 250/370.11 X |
| 5,596,198 | 1/1997 | Perez-Mendez | 250/370.11 |

FOREIGN PATENT DOCUMENTS

| | | | |
|---|---|---|---|
| 2-83489 | 3/1990 | Japan | 250/370.11 |
| 5-256950 | 10/1993 | Japan | 250/370.11 |

*Primary Examiner*—Edward J. Glick
*Attorney, Agent, or Firm*—Darby & Darby, P.C.

[57] ABSTRACT

An imaging detector includes a collimator, a scintillator and a photodiode array. The collimator directs radiation to scintillator segments having apertures substantially matched to collimator apertures. Optical reflectors and heavy metal septa between the segments reduce light and radiation scatter between the segments, respectively. Photodiode array elements with active areas substantially matched to the scintillator segment apertures detect light generated when the radiation interacts with the scintillator. A cooler, a low noise photodiode array and readout electronics improve the signal-to-noise ratio of the imaging system in specific embodiments.

32 Claims, 5 Drawing Sheets

RADIATION IMAGING DETECTOR

BACKGROUND OF THE INVENTION

The present invention relates to radiation imaging and, more specifically, to a radiation imaging detector incorporating a collimator, a scintillator and a photodiode array.

Radiation imaging systems typically are used to generate images of the distribution of radiation either transmitted through an object or emitted from an object. Such radiations are not of themselves visible to the naked eye. The various modalities of imaging distributions of radiation include Transmission Imaging and Emission Imaging. Both of these modalities are applied in medicine. Classical transmission imaging or X-ray radiography is a technique wherein the radiation is generated externally and caused to propagate through an organ or body to the detector. In this way an image of the distribution of radiation absorption (transmission) in the organ or body is obtained.

In emission imaging ("Nuclear Medicine"), radiation is generated within the organ by a radiopharmaceutical or other radiation bearing substance which passes through or in some cases is designed to accumulate in the organ. Many emission imaging applications exist including single photon planar imaging and Single Photon Emission Computed Tomography (SPECT) for imaging the structure or function of internal organs. An example of this is CARDIOLITE™ (Tc-99m-Sestamibi) cardiac imaging. Gamma-ray cameras employed in single photon emission imaging applications typically consist of a collimator for "focusing" the gamma rays, a detector for determining the position of each incident gamma-ray and a device for displaying the acquired images.

Preferably, a detector for a single photon emission imaging system has high spatial resolution and high energy resolution. High spatial resolution is required to image small features. High energy resolution is required to discriminate against the large number of photons which are scattered and which therefore might be measured in the detector at erroneous positions. Because some energy is lost in the scattering process the scattered photons have reduced energy. These scattered photons may be eliminated if sufficient detector energy resolution is available to identify the reduction in photon energy which occurs in the scattering process.

The gamma-ray energies in single photon emission imaging typically are between 80 keV and 400 keV. A further reason for the high energy resolution requirement is that the signals for low energy (e.g., 140 keV photons) imaging systems are small, and a high signal-to-noise ratio is required to separate the signals produced by detection of gamma rays from the noise present in the imaging system. Single photon emission imaging is treated in Chapter Eight of the book entitled "Medical Imaging Systems," by A. Markovski, published in 1983 by Prentice Hall, New Jersey.

A second type of emission imaging in Nuclear Medicine is dual photon imaging such as Positron Emission Tomography (PET). In PET imaging, two coincident and oppositely traveling gamma-rays, each with energy of 511 keV, are produced by positron annihilation. In this case, a camera system is required which can detect the two photons in coincidence. In addition, because PET applications typically use higher energy radiation than single photon imaging applications, higher noise can be tolerated for similar system signal-to-noise ratio.

One single photon medical diagnostic application, referred to as "Scintimammography," involves the injection of tumor seeking radiopharmaceuticals in order to facilitate the identification and quantification of the presence of such tumors. In this case the radiopharmaceutical includes a gamma-ray producing isotope (Tc-99m). Planar or tomographic views of the organ from this type of radiation imaging enables a doctor to view the organ without subjecting the patient to the trauma associated with a biopsy. Scintimammography is described in papers titled "Scintimammography: the complementary role of Tc-99m Sestamibi prone breast imaging for the diagnosis of breast carcinoma," by I. Khalkhali, J. A. Cutrone, I. G. Mena, L. E. Dingles, et al., published in 1995 in Radiology, Vol. 196, and "Technetium-99m-sestamibi uptake in breast tumor and associated lymph nodes," by J. Maublant, M. de Latour, D. Mestas, et al., published in 1996 in the Journal of Nuclear Medicine, Vol. 37.

To generate an image of the organ using one of the above techniques, a detector is used to measure the radiation which propagates from the organ through the rest of the body, the air and any other medium in between the body and the detector until it impinges on the detector. The radiation interacts with the detector to generate electrical signals representative of the detected radiation. The electrical signals can then be processed to generate an image on a video display device such as a computer monitor.

One method of generating electrical signals from detected radiation uses a scintillator and a photodetector. The scintillator is composed of a material that absorbs radiation of specified energy (for example, gamma radiation of 140 keV or 511 keV) and converts it to visible light. The photodetector, in turn, converts the light emitted by the scintillator into electrical signals. This method is discussed in Chapters 8–10 of a book titled "Radiation Detection and Measurement, 2nd Edition" by Glenn F. Knoll, published in 1989 by John Wiley and Sons, Inc.

Conventionally, displayed images consist of either a two- or three-dimensional pattern of image representation. To generate a two-dimensional image of an organ, a two-dimensional pattern of radiation information must be detected. Three-dimensional images are typically constructed from multiple two-dimensional projections using a computer to perform tomography.

Specific requirements on image quality are dependant on the particular application, however, in general the quality of an image can be measured by the signal-to-noise ratio of the observed features in the image, by the contrast in the image and by the detail of the structure that can be observed in the image. The basic physical parameters that influence the image quality in this way are (1) the system spatial resolution (2) the certainty as to the values of each pixel in the image, and (3) the ability of the system to distinguish between the signal and anomalous or artifactual features which degrade the image quality.

The system spatial resolution is a measure of the fineness of the features that can be distinguished in the object being imaged. The system spatial resolution can only be modified through the design of the system including choice of components, the intrinsic resolution of the various components (such as the collimator, scintillator and photodetector array), and the way that the components are arranged in the detector configuration.

The certainty ascribed to the pixel values is a function of the statistics in the image acquisition which can be affected by altering the duration of the imaging procedure, or by proximity of the object being imaged to the detector. By orienting the detector proximally to the organ being imaged the solid angle can be reduced thus increasing the radiation flux.

The ability of the imaging system to discriminate against undesirable anomalous or artifactual features (such as scatter, blurring, etc.) is dependant on the inherent ability of the system to identify differences between the "true" signal and the undesired features. Blurring and signal-to-background degradation arise from many sources of scatter and background radiation. The main source of background radiation occurs due to uptake of the radiopharmaceutical in surrounding tissues and organs. This background radiation has a degrading effect on image quality. One way to suppress the background radiation is by close proximity of the detector to the organ being imaged thereby eliminating the rest of the body as background. Sources of scatter include Compton scatter in the body itself (both the organ being imaged and other organs, bones, etc.), scatter from various media in and around the body, scatter from the aperture (collimator), other parts of the imaging system, and scatter within the detector (including scintillator and photodetector). Other sources of anomalous radiation include emission of X-ray fluorescent radiation (such as escape X-rays) from the materials in the collimator, scintillator and photodetector. Each of these can significantly degrade the image. However, because such radiations occur at energies different (longer wavelengths) from that of the original radiation, if the detector design has sufficient fidelity to assess the incoming photon's energy it can be eliminated by such discrimination.

Traditional gamma cameras as discussed above are general purpose instruments used for whole-body as well as isolated organ studies. Conventionally, gamma camera applications have been limited to scintillation imaging detectors which utilize photomultiplier tubes (PMT's) for detecting the light emitted from the scintillator. This development is described in a paper titled "Scintillation Camera," by Hal O. Anger, published 1958, The Review of Scientific Instruments, Vol. 29 No. 1. The modern gamma-camera described in a paper titled "Gamma-Camera Systems," by M. D. Short, in 1984, Nuclear Instruments and Methods, Vol. 221 which follows the art has an imaging head (including parallel hole collimator, scintillator, PMT's and enclosure) which is typically 40 cm in diameter, it has a large depth, and it is very bulky. Such systems typically weigh over 1000 lbs. The camera head typically employs a parallel-hole collimator composed of a lead sheet (or other material with a high atomic number) with parallel holes for collimating the incident radiation. The standard commercially available high resolution (HiRes) gamma camera utilizes hexagonal holes with 1.5 mm hole diameter and 4 cm length. The scintillator is generally a single crystal (70 cm dia.) which is coupled to multiple PMT's. Each PMT covers several square centimeters of the total area of the scintillation crystal. The location of radiation interaction in the crystal is determined by comparing the amount of light collected in each of the PMT's in order to estimate the position of interaction.

The intrinsic spatial resolution of the existing gamma-camera is limited to about 4 mm due to the constraints of the particular technology employed. However, due both to this inherent limitation and to its large size which prevents positioning proximal to the organ being imaged, the system resolution under typical conditions for scintimammography typically limits the procedure to tumor sizes greater than 1 cm.

In addition, inherent limitations of the technology for the existing gamma camera typically limits the energy resolution to worse than 10%.

Due to the limitations of the PMT based prior systems, certain other technologies based upon the concept of replacing either the scintillator and PMT or the PMT alone with solid-state detectors are under investigation. Where the scintillator and PMT are both eliminated, the replacement is most typically a solid-state detector which directly converts the radiation into electrical signals.

Of the direct detectors, certain technologies have been immediately dismissed because they require cryogenic cooling which is not practical to achieve in combination with the imaging requirements. The technologies requiring cryogenic cooling include High Purity Germanium (HPGe) and Lithium drifted Silicon (Si[Li]) as examples. A paper titled "A Multi Detector Germanium Gamma Ray Camera," by D. Miller, P. Schlosser, A. Deutchman, et al., published in 1979, IEEE Transactions on Nuclear Science, Vol. NS-26, No. 1, describes a Germanium gamma-ray camera. Newer room temperature high-atomic-number compounds could be employed including Cadmium Telluride based compounds (CdTe) and Mercuric iodide ($HgI_2$). Certain implementations of these technologies can offer some superior performance specifications to the prior gamma-camera art, however, limitations of these devices include very high cost due to low yields of high-quality crystals, and certain deficiencies in other performance specifications due to inherent deficiencies of the compounds in the collection of the signal. The description of a $HgI_2$ based gamma camera is described in the paper "Multi-Element Mercuric Iodide detector Systems for X-Ray and Gamma-Ray Imaging," by B. E. Patt, published in 1993, Material Research Society Symposium Proceedings, Vol. 302, published by the Materials Research Society. The description of a CdTe based gamma camera is described in the paper titled "An Array of CdTe Detectors for Imaging Applications," by Y. Eisen and E. Polack, published in 1993, Material Research Society Symposium Proceedings, Vol. 302, published by the Materials Research Society.

Where the scintillator is still employed and only the PMT is eliminated, the replacement for the PMT may be a solid-state detector which converts the light emanating from the scintillator into electrical signals.

Use of $HgI_2$ photodetectors to read the light signal from scintillators has been shown by Y. J. Wang, B. E. Patt, J. S. Iwanczyk, S. R. Cherry, and Y. Shao, in a paper titled "High Efficiency CsI(Tl) /HgI2 Gamma Ray Spectrometers," published in 1995, IEEE Transactions on Nuclear Science, Vol. 42, No. 4. In this case a very exotic compound semiconductor photodetector is used. Another approach utilizing CsI(Tl) scintillators in conjunction with silicon photodiodes to make gamma-ray detectors has been described by A. J. Bird, T. Carter, D. Ramsden, and B. M. Swinyard, in a paper titled "The Optimization of Small CsI(Tl) Gamma-Ray Detectors," published in 1993, IEEE Transaction on Nuclear Science, Vol. 40, No. 4. The electronic noise level and resultant energy resolution for gamma-ray detection in this art are not sufficient for single photon medical imaging applications.

Thus prior systems as discussed above typically have poor spatial resolution and low signal-to-noise ratio. The poor spatial resolution makes it difficult to distinguish small features in the image. The poor signal-to-noise ratio makes it difficult to distinguish electronic component noise and energy associated with scattered radiation from the energy associated with radiation directly entering into the crystal. In addition, conventional systems are large in size and bulky, making them difficult to place in close proximity to the organ being imaged. This limits the spatial resolution and lowers the number of photons incident on the detector, while simultaneously increasing the unwanted background radiation. As a result of these factors, important image detail may be lost. Thus, a need exists for an imaging detector that provides higher quality images.

SUMMARY OF THE INVENTION

The imaging detector of the present invention utilizes a collimator, a scintillator and a photodiode array in combination to maintain the spatial relationship of radiation entering the imaging detector and to accurately measure the energy level of the radiation. The imaging detector components are constructed and positioned to control the propagation of the radiation and the light through the imaging detector. As a result, radiation entering the imaging detector over a given area is detected by the scintillator/photodiode element that is physically aligned with that area. The result is that very high spatial resolution can be achieved. The intrinsic spatial resolution of the preferred embodiment is 1.75 mm.

The entrance of radiation into the imaging detector is controlled by the collimator. The collimator consists of parallel chambers with walls parallel to the desired direction of propagation. The walls preferably contain a heavy metal, e.g., tungsten, to prevent radiation from propagating between the chambers. Thus, after the radiation enters the imaging detector, the majority of the radiation propagates through the chambers in a direction substantially parallel to the chamber walls.

The scintillator is aligned to receive radiation that has propagated through the collimator. In one embodiment, the scintillator consists of numerous segments each of which are physically aligned with a respective collimator chamber. Optical reflectors between the scintillator segments reflect light back into the segment. Heavy metal septa prevent radiation from propagating between the segments.

Each element in the photodiode array is physically aligned with a respective scintillator segment to detect light produced by the interaction of radiation with that element's scintillator.

Thus, the present invention maintains substantial alignment between the path of propagation of the radiation that enters the imaging detector and the path of propagation of the light that interacts with the photodiode. Radiation that enters a given collimator chamber will propagate to a specific segment of the scintillator and will be detected by the photodiode associated with that segment.

By aligning the imaging detector components and matching their physical cross-sections, the present invention may provide an imaging detector which improves the signal-to-noise ratio for each radiation event, which improves the spatial resolution over prior systems, and which also reduces the crosstalk compared with conventional imaging detectors. These factors result in better image quality of the displayed image.

Additional features can be provided to improve the signal-to-noise ratio of an imaging detector constructed according to the invention. For example, low noise photodiodes and readout electronics can be utilized. A cooler can also be provided for cooling the photodiode array and readout electronics to reduce inherent electronic noise. As a result, the system can more effectively distinguish between valid radiation signals and system noise or radiation that should be associated with a different photodiode element.

In a preferred embodiment of the imaging detector of the present invention, it is used to realize a new type of gamma-camera for Scintimammography wherein its use will result in improvements in performance over prior systems.

The detector technology may provide improvements in both spatial and spectral (energy) resolution over existing detectors. The improvement in spatial resolution over existing nuclear medicine gamma cameras is the result of the better intrinsic detector resolution and optimized collimator optics as discussed. Improvement in spectral (energy) resolution is due to improved signal-to-noise ratio for each radiation event of the present invention. The size of the camera will be small relative to prior systems which will enable optimal orientation relative to the breast and be used in conjunction with partial compression for further improvement in spatial resolution as well as improvement in geometric efficiency. The closer orientation with respect to the rest of the body, the partial breast compression, and the improved energy resolution combined with the ability thereby to eliminate scatter and other anomalous events will significantly reduce image background and image noise. This can be understood if one considers the difficulty of positioning a 70 cm diameter, 1000 lb. standard gamma camera, compared with the ease of positioning a 10–15 cm diameter camera proximal to the breast for imaging from the lateromedial and medial-lateral vantage point in such a way that radiation from the body would not contribute to the background.

These factors may result in significant improvements over prior gamma-camera systems in each of the critical areas for breast imaging, namely: order of magnitude improvement in geometric efficiency; factor of 2 improvement in spatial resolution for buried tumors; factor of 3.4 reduction in either of required acquisition time or dose for same count density in the Field of View as required for prior gamma-cameras. Additionally, the truly compact nature of the camera compared with even the smallest prior systems will allow a reduction in weight burden.

Accordingly, an imaging detector of the present invention includes: a collimator including a plurality of chambers, each chamber having an end defining an exit aperture cross section; a scintillator including a plurality of segments, each segment having a first end defining a first aperture cross section substantially matching one of said exit aperture cross sections and having a second end defining a second aperture cross section; and a photodetector array including a plurality of elements, each element having a cross section substantially matching one of said second aperture cross sections.

In an alternate embodiment, when a lower energy radiation source is utilized, the scintillator septa are omitted because there is less crosstalk between the segments.

BRIEF DESCRIPTION OF THE DRAWINGS

The above and other features of the present invention may be more fully understood from the following detailed description, taken together with the accompanying drawings, wherein similar reference characters refer to similar elements throughout and in which.

DESCRIPTION OF THE PREFERRED EMBODIMENT

Figure 1:
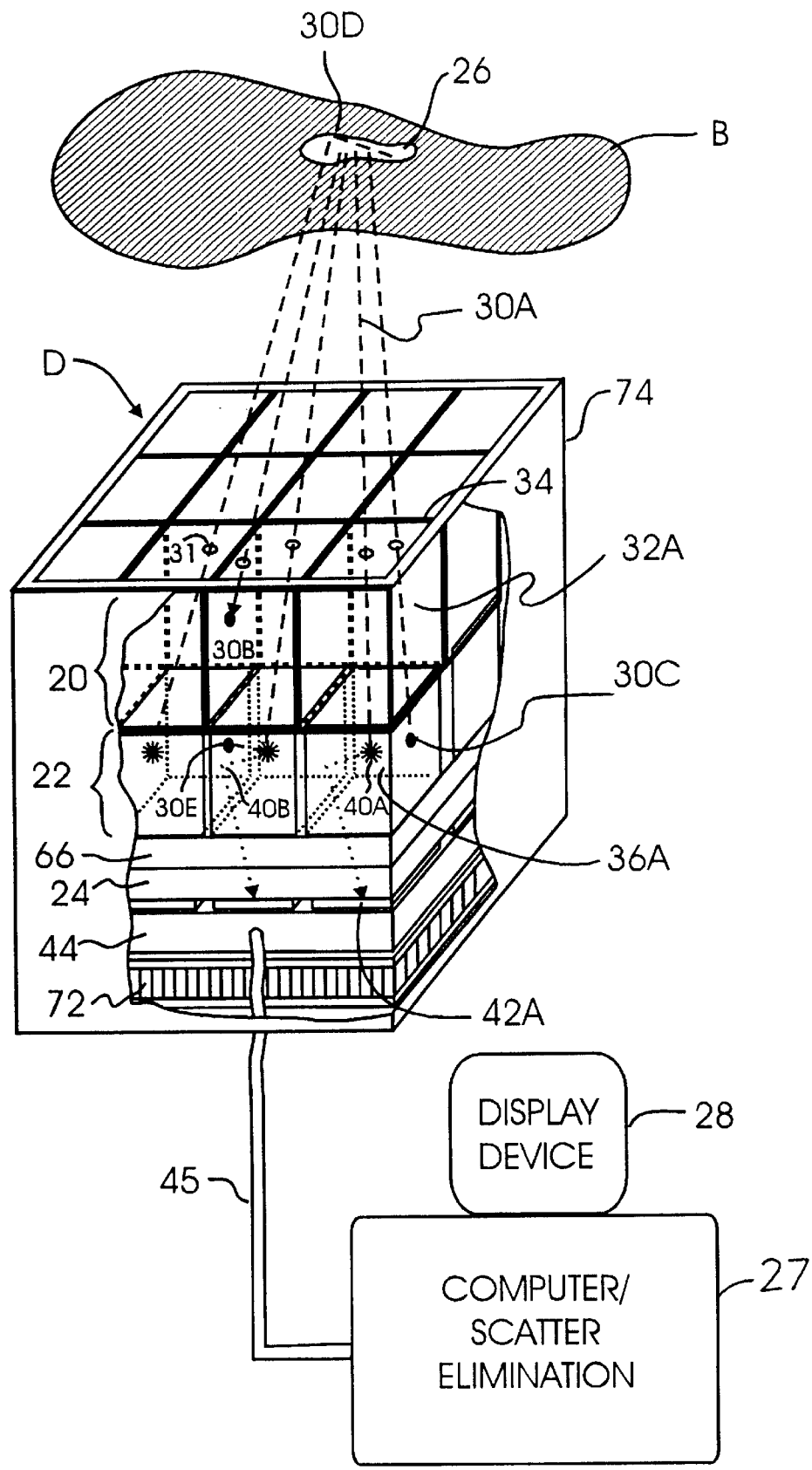
FIG. 1 is a diagrammatic perspective view of an imaging system constructed in accordance with a first embodiment of the present invention, showing the system in use with a suitable radiation source.

Referring to FIG. 1, one embodiment of an imaging detector D having a collimator 20, a scintillator 22 and a photodiode array ("PDA") 24 detects radiation from a radiation source 26. The imaging detector D produces signals that are processed by additional electronics, scatter reduction electronics (or software), and a computer system 27 to generate images on a display device 28.

To preliminarily consider the function of the disclosed embodiment, radiation 30A from a radiopharmaceutical or other radiation source 26 in the body B propagates through a body B and enters the top of a chamber 32A of the collimator 20 (imaginary circles, e.g., 31, show the entry point of the radiation into the imaging detector and are for illustrative purposes only). The chamber walls 34 preferably contain a heavy metal to reduce the likelihood that radiation colliding with a chamber wall 34 will propagate to an adjacent chamber, being absorbed by the chamber wall 34 instead.

The cross section of the exit aperture of the collimator chamber 32A is matched to the cross section of a corresponding scintillator segment 36A. This ensures that radiation (e.g., 30A) exiting the bottom of the chamber 32A interacts with the scintillator segment 36A that is directly below the chamber 32A. The space 64 (FIG. 2) between adjoining scintillator segments 36A and 36B also contains a heavy metal to reduce the likelihood that primary radiation scattered radiation (due to scatter in the scintillator segments 36A and 36B), and secondary radiation (due to emission of escape X-rays) will propagate from one segment to another.

The interaction of the radiation 30A with the scintillator segment 36A produces a light pulse 40A. Optical reflectors (not shown) surrounding the segment 36A on the sides and top prevent the light pulse 40B from propagating to adjacent segments.

The cross section of the scintillator segment 36A is matched to the cross section of a corresponding photodiode element 42A of the photodiode array 24. This ensures that light exiting the bottom of the scintillator segment 36A impinges upon the photodiode element 42A that is directly below the scintillator segment 36A. The photodiode element 42A converts the light into electrical signals that are amplified by readout electronics 44 and sent to the additional electronics and computer 27 over a line 45 before displaying on display device 28.

Figure 2:
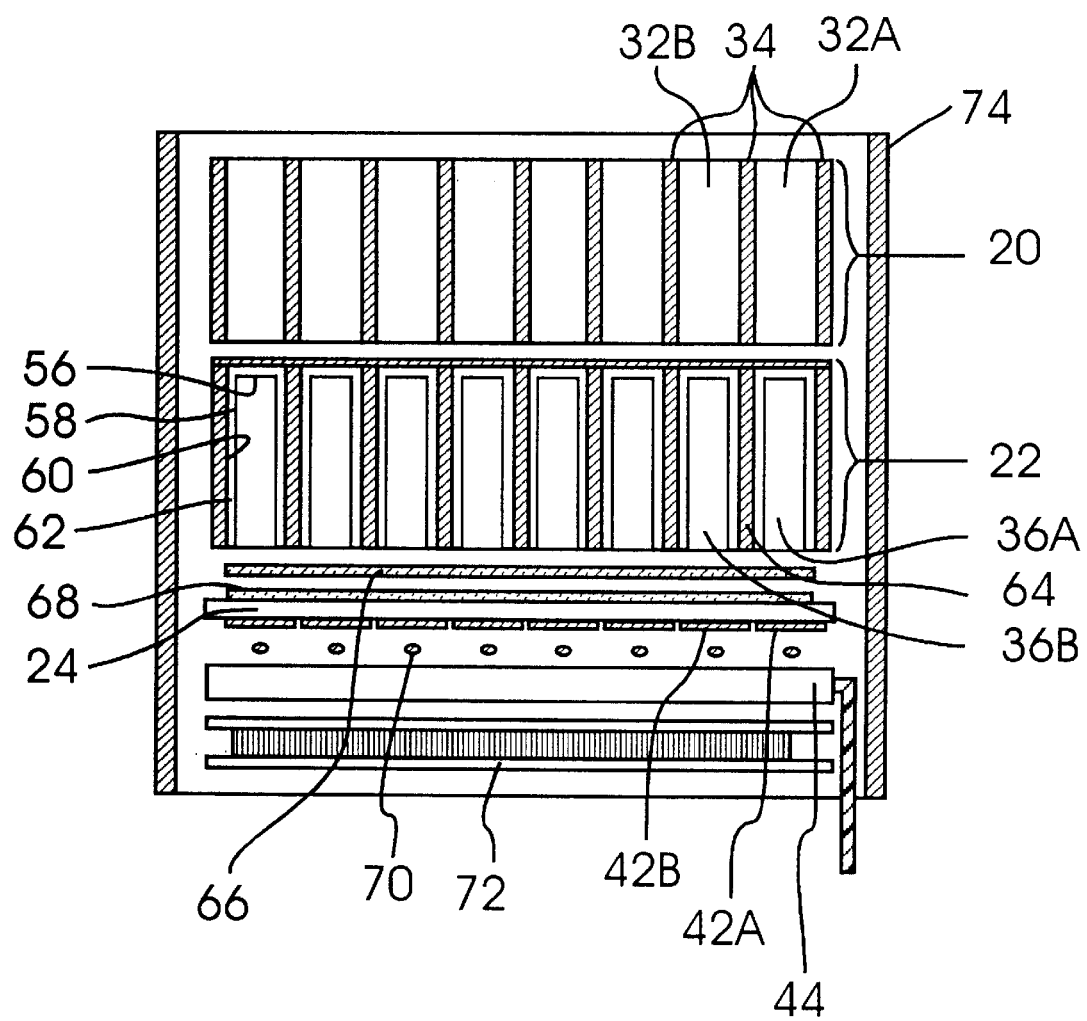
FIG. 2 is a partial vertical sectional view of a detector of an imaging system constructed in accordance with the present invention, shown in exploded form.

Considering the components of the imaging detector D in more detail, FIG. 2 illustrates a partial vertical sectional view of an imaging detector having eight elements (for the collimator, scintillator etc.) on a side (in practice, the number of elements used will depend on the requirements of the application and can be arranged in, for example, an N×M rectangular configuration where N and M are integers; for example, in FIG. 1, an imaging detector with a 3×4 configuration is shown). The collimator 20 has an array of chambers (e.g., 32A and 32B) defined by chamber walls 34. The chamber walls 34 are constructed of material having a high atomic number, such as tungsten or lead in order to limit septal penetration. Typically, radiation incident a chamber wall 34 (e.g., radiation 30B, FIG. 1) is absorbed by the chamber wall before it passes through to an adjacent chamber. Thus, the chamber walls 34 help ensure that only radiation which comes directly into the top of a chamber and which is propagating in a direction which is ostensibly parallel to the chamber walls 34 (e.g., 30A) exits the bottom of the chamber to the scintillator segment (e.g., 36A) below.

Figure 3:
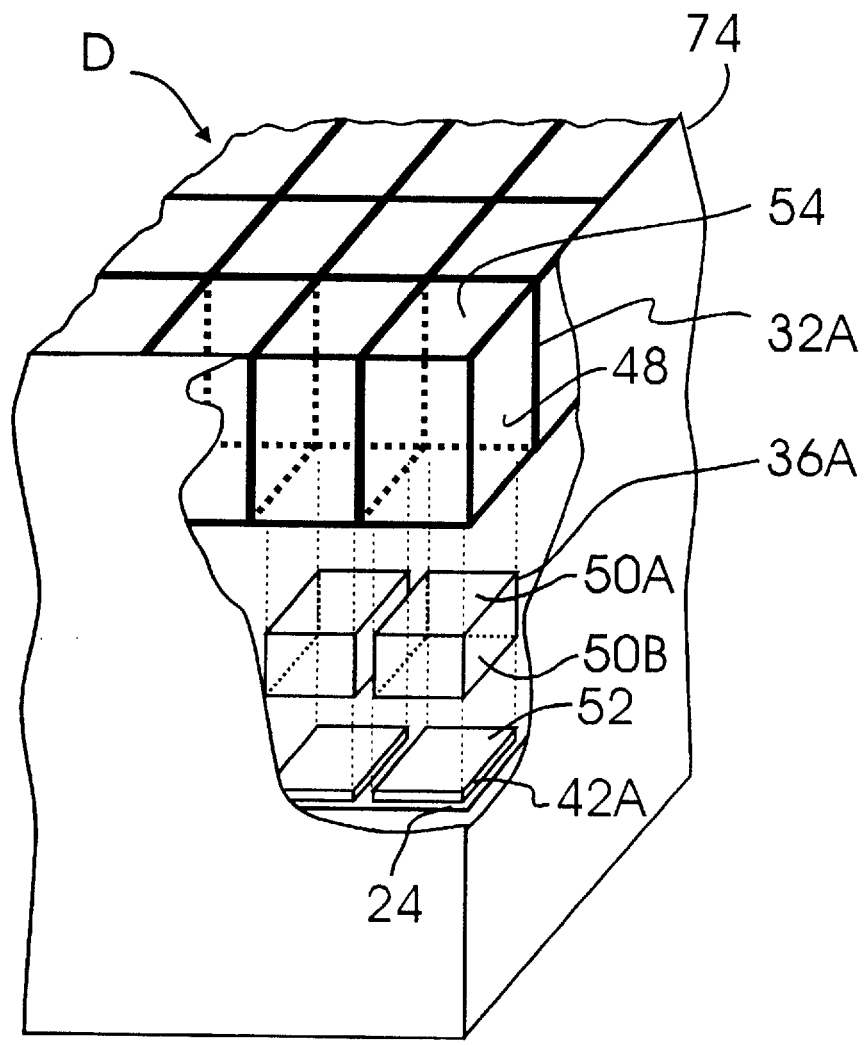
FIG. 3 is a fragmentary, exploded perspective view illustrating, in simplified form, the substantially matching cross sections of the collimator, the scintillator and the photodiode array of the imaging system of FIG. 1.

Referring now to FIG. 3, the cross section 48 of the exit aperture of the collimator chamber 32A, the cross sections 50A and 50B of the upper and lower surfaces of the scintillator segment 36A, and the cross section 52 of the photodiode element 42A, are matched. A tolerance on the order of tens of microns is typical. Significantly, by using matched cross sections, the intrinsic spatial resolution of the imaging detector D may be predominantly defined by the geometry of these components for gamma-ray (or X-ray) energies up to a few hundred thousand electron volts.

Other dimensions of the collimator 20 may vary depending on the requirements of the particular application. Typically, the collimator 20 is between 1 cm and 4 cm long, and the scintillator 22 is long enough to assure about 67% or more attenuation of the incoming gamma-rays (approximately 4 mm for 140 keV in CsI[Tl]). The thickness of the chamber walls 34 is generally between 50 micro meters and 500 micro meters.

The collimator chambers (e.g., 32A) can have cross sections in any of a variety of shapes, including square, round and hexagonal. Altering the shape of the cross section can improve the fill factor (i.e., reduce dead space between chambers).

The overall shape of the collimator 20 and, in particular, the entrance side 54 (FIG. 3) facing the radiation source is optimized for a specific organ or other body B to be imaged. Furthermore, parallel, converging and diverging collimators can be used interchangeably with the other components of the imaging detector D.

As shown in FIG. 1, the collimator 20 is closely coupled and aligned with the scintillator 22. In a preferred embodiment, the scintillator 22 is an array constructed from individual scintillator segments 36A and 36B (FIG. 2). Each of the segments has optimally prepared surfaces. The top 56 is roughened and the sides 58 are highly polished.

Each scintillator segment (e.g., 36A) is surrounded on its sides and its top by an optical reflector 60 that is spaced from the segment by an air gap 62. The optical reflector 60 reflects light (e.g., 40B, FIG. 1) back into the scintillator segment that produced it. Typically, the optical reflector 60 consists of an epoxy doped with titanium dioxide.

In one embodiment, the scintillator 22 is made from a CsI[Tl] compound. The wavelength of the compound is selected to match the response of the photodiode array 24 as closely as possible. Other compounds, such as CsI[Na], NaI(Tl), YSO, LSO, GSO and BGO, may also be used depending on system design requirements.

The inter-segment spaces 64 incorporate high atomic number septa (e.g., tungsten or lead). These septa impede the propagation of radiation (e.g., 30C and 30E, FIG. 1) to minimize radiation crosstalk between elements (e.g., 36A and 36B, FIG. 2) in the scintillator array 22.

The scintillator 22 is coupled to the PDA 24 by an optically transparent thermal layer 66 (FIG. 2). The refractive index of the thermal layer 66 is chosen to minimize light lost by internal reflection at the interface between the scintillator 22 and the PDA 24. Typically, the thermal layer 66 consists of an epoxy. However, an air coupling may be used in some applications.

When it is desired to cool the PDA 24, the thermal characteristics of the thermal layer 66 are selected depending on the thermal dependance of light output of the scintillator material being used. If the light output of the scintillator material (e.g., BGO) increases with decreasing temperature, a thermally conductive thermal layer 66 may be employed. If the light output of the scintillator material (e.g., CsI[Tl]) decreases with decreasing temperature, a thermally insulating thermal layer 66 may be employed.

The PDA 24 consists of an array of photodiode elements 42A and 42B (commonly referred to as pixels). The array may be assembled from a plurality of individual photodiodes or, in a preferred embodiment, can be formed on a monolithic silicon wafer. Generally, higher photodiode density can be achieved using a single silicon wafer.

The photodiode structure for each pixel is a P-I-N photodiode formed on high resistivity silicon utilizing planar processing technology. Gettering techniques are used to increase the lifetime of minority carriers and lower the leakage currents in the bulk. Surface passivation is utilized to lower the surface leakage currents. Overall leakage current is preferably below 5 nA/cm$^2$. Accordingly, the imaging detector D produces very little electronic noise and has a very good signal-to-noise ratio.

The entrance electrode (not shown) of the photodiode structure is optimized to receive light from the scintillator 22. In addition, the surface of the PDA 24 is covered with an anti-reflective coating 68 to maximize the quantum efficiency of the PDA 24. Typically, a quantum efficiency higher than 70% is obtained for a scintillator material such as CsI(Tl) when these techniques are employed.

The PDA 24 is closely coupled to the readout electronics 44. In an embodiment with a narrow probe rendition requiring vertical assembly, a bump bond 70 (FIG. 2) may be used. Bump bonds 70 provide good electrical and thermal transfer characteristics and permit many contacts to be made in a relatively small area. Bump bonding also provides a relatively small distance between the PDA 24 and the readout electronics 44, thereby minimizing stray capacitance.

The bump bonds 70 may be any size or shape. Typically, the bonding pads are round dots 20–50 microns in diameter. Indium is a commonly used material for the bump bonds 70.

In an embodiment where a flat geometry (horizontal assembly) is preferred, a low stray capacitance fan-out (not shown) may be used in place of bump bonds. The fan-out is optimized to match the outputs of the PDA 24 and the inputs of the readout electronics 44. Preferably, the stray capacitance for the fan-out will be less than 3 picofarad.

The readout electronics 44 typically consists of a low noise integrated circuit that has individual channels to provide amplification for each pixel of the PDA 24. Each channel consists of a low-noise, high-gain, charge-sensitive preamplifier followed by a shaping (amplifier) network. The design and construction of suitable readout electronics will be appreciated by a worker in the art based on the description herein, and therefore are not dealt with here in detail.

The input capacitance of the readout electronics 44 is matched to the input capacitance of the photodiodes. Typically, noise levels less than 40 e$^-$ RMS are obtained at −15° C.

A variety of readout electronics configurations may be used. For example, one or more channels may be contained in a single component. Alternatively, individual fan-out contacts may be used. If desired, the signals can be multiplexed to reduce the associated wiring complexity.

A cooler 72 may be implemented using a liquid circulating cooler or a thermoelectric cooler, such as a Peltier device. A Peltier device is preferred because it is self-contained and does not vibrate.

Cooling reduces the electronic noise in the PDA 24 and the readout electronics 44. In embodiments that use a very low noise silicon PDA, the cooler 72 may be omitted. Otherwise, cooling is especially important for the PDA 24. In a typical application, the PDA 24 is maintained at a temperature of −15° C.

The thermoelectric cooler of the invention uses electronic feedback to maintain the critical imaging detector components (PDA 24) and the readout electronics 44 at a constant temperature. This provides stable response independent of the ambient temperature or any contact between the imaging detector D and a patient's body.

The imaging detector D includes an enclosure 74 (typically made of stainless steel) which can be easily sterilized using chemical sterilization techniques. The inside 76 (FIG. 4) of the enclosure 74 is preferably maintained at a vacuum or is filled with inert gas such as dry N$_2$ to prevent water condensation on cold surfaces.

The imaging detector D is optimally designed to detect radiation from a radiation source 26 (FIG. 1) that produces radiation in the 140 keV range. Generally, the imaging detector D is used to image gamma rays. However, the imaging detector D may be used to perform X-ray imaging in some applications. In a typical application, the radiation source 26 is either mono-energetic or produces several distinct energy levels.

The disclosed embodiment provides an improved imaging detector in several respects. Typically, the imaging detector D provides energy resolution better than 10% fwhm at 140 keV, low noise threshold lower than 30 keV, intrinsic spatial resolution better than 2.0 mm fwhm at 140 keV and radiation efficiency exceeding 67% at 140 keV. These performance characteristics have not heretofore been obtained in an imaging detector.

The use of components with low signal-to-noise ratios and the cooling of selected components improves the energy resolution of the imaging detector D. As a result, the imaging detector D can more effectively identify and eliminate signals produced by scattered radiation (e.g., 30D and 30E, FIG. 1).

This results in better signal-to-noise ratio in the image which in turn allows one to faithfully discern smaller structures and features in the image.

The collimator and scintillator septa significantly reduce the likelihood that scatter and secondary radiation from the rest of the body, from other media in the vicinity of the body, from the components of the imaging system, as well as the detector itself will become part of the imaged information. As a result, the spatial resolution in the disclosed invention is improved (perhaps as much as an order of magnitude over the spatial resolution of prior devices) because the scintillator and the PDA element can more effectively detect radiation that directly enters the corresponding collimator chamber. Thus, the contrast of the displayed image is significantly improved.

Furthermore, the disclosed embodiment can be used in small gamma-cameras for medical diagnostics that can be positioned closer to the organ being diagnosed. This provides a better signal-to-noise ratio and spatial resolution than existing methods.

Figure 5:
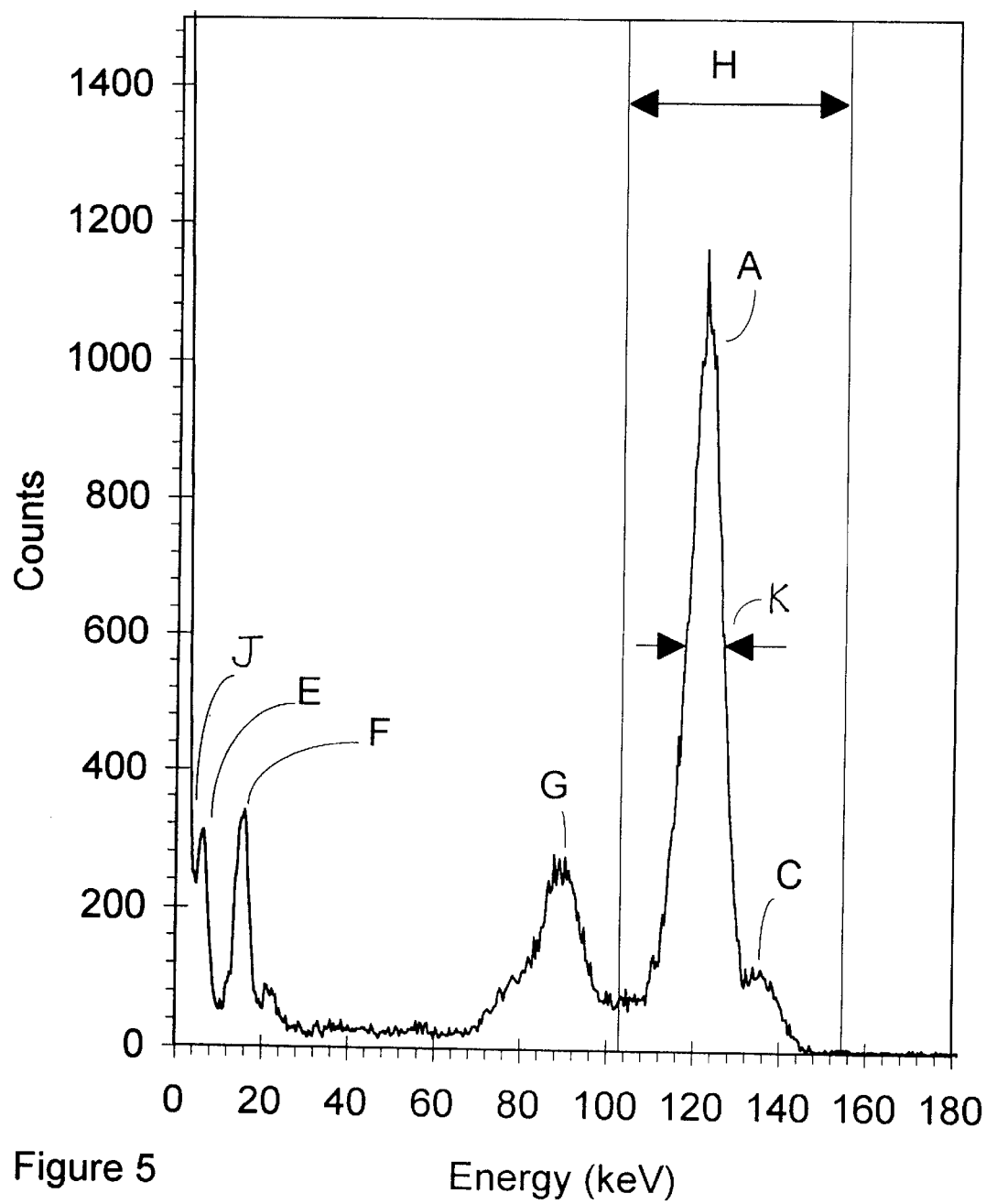
FIG. 5 is an energy spectrum for a Co-57 radiation source measured with a prototypical single segment of an imaging system constructed in accordance with a first embodiment of the present invention.

Referring to FIG. 5, the energy resolution K for the photopeak A corresponding to gamma-rays of energy 122 keV is 7.5% Full Width at Half Maximum (FWHM). This result is possibly better than any energy resolution previously reported in the literature for the 122 keV photopeak measured with a scintillator detector of any sort. This improvement is due to the physical principles of operation outlined for the present invention. The photopeak C for the 136 keV gamma-ray (which occurs in addition to the 122 keV emission as part of the Co-57 decay scheme) is also visible as a shelf on the right side of the 122 keV photopeak A. In addition, Cesium and Iodine escape peaks G, the 14.4 keV Co-57 gamma-ray photopeak F and the 6.4 keV Iron characteristic X-ray radiation photopeak E are clearly visible. The visibility of the 6.4 keV photopeak E is due to the extremely low noise cutoff J of about 3.7 keV. In the implementation for the preferred embodiment of the present invention the demonstrated low electronic noise and resultant high energy resolution will allow rejection of unwanted lower energy radiation and acceptance of signal only in the required energy region H. This can be accomplished via an electronic circuit or software means.

The present invention is useful in numerous applications. For example, scintimammography; scintigraphy for other organs; interoperative probes; Single Photon Emission Computed Tomography (SPECT); Computer Aided Tomography (CAT); imaging radionuclide distribution in waste or warheads; imaging of electronic or mechanical parts for process control, quality control, fatigue or delamination; guided systems for nuclear materials or waste retrieval or removal; and portable imaging systems.

Figure 4:
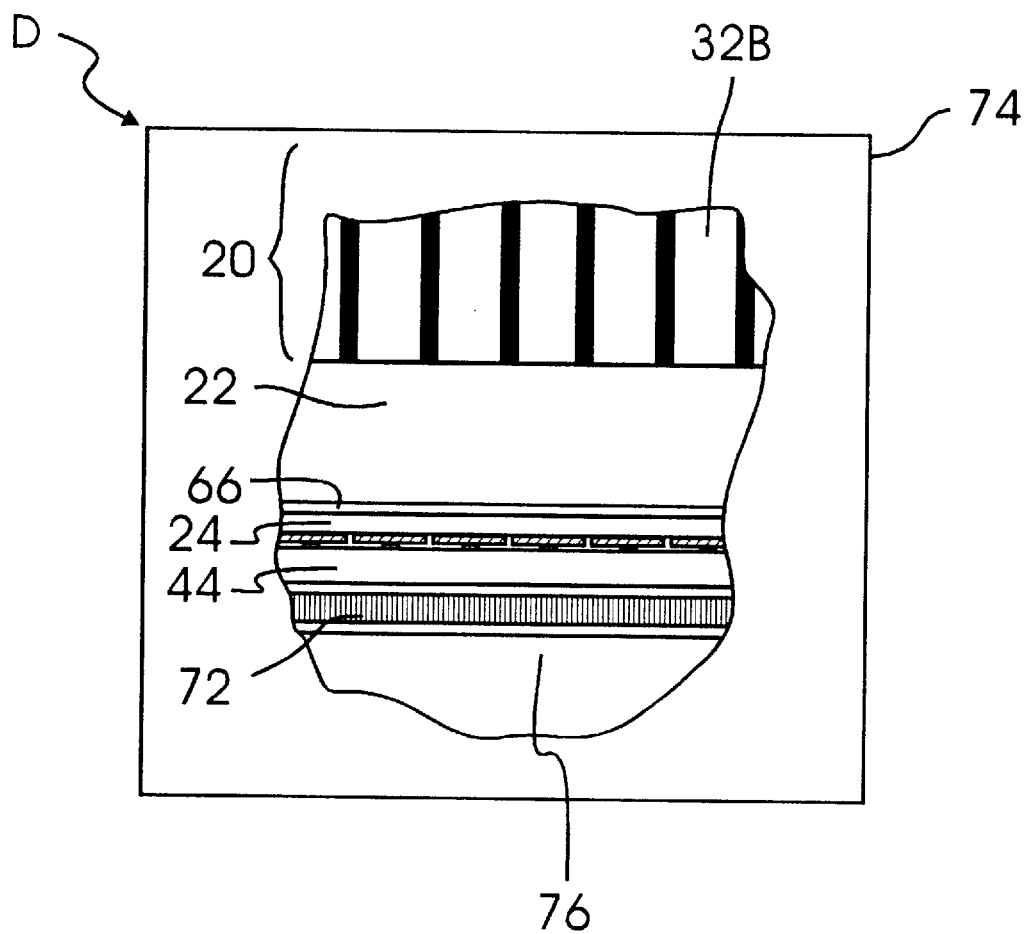
FIG. 4 is a side elevational view, partially broken away, of an imaging system constructed in accordance with a second embodiment of the present invention.

In an alternate embodiment, a lower energy radiation source is used. In this embodiment, the radiation does not scatter as much because it is readily absorbed by the scintillator 22. Thus, the scintillator septa can be omitted because there is less crosstalk between the segments. This embodiment is depicted in FIG. 4 where a non-segmented scintillator 22 is employed. This embodiment can provide effective imaging at lower cost in some circumstances.

From the above, it can be seen that the present invention provides an improved imaging detector.

While certain specific embodiments of the invention are disclosed as typical, the invention is not limited to these particular forms, but rather is applicable broadly to all such variations as fall within the scope of the appended claims. For example, a wide variety of collimator structures, scintillator materials, photodetectors, readout electronics, coolers, couplers and bonding methods may be used. Thus, the specific structures discussed in detail above are merely illustrative of a few specific embodiments of the invention.

What is claimed is:

1. An imaging detector for collimating and detecting individual x-ray or gamma-ray photons, comprising:
   a collimator including a plurality of chambers, each chamber having an end defining an exit aperture cross section;
   a scintillator including a plurality of segments, each segment having a first end defining a first aperture cross section substantially matching one of said exit aperture cross sections and having a second end defining a second aperture cross section;
   a photodetector array including a plurality of elements, each element having a cross section substantially matching one of said second aperture cross sections; and
   an array of readout electronics channels for amplification and processing of electrical signals produced by said photodetector array, each channel being coupled for communication with a respective one of said photodetector array elements.

2. An imaging detector according to claim 1 further including optically reflective septa positioned between said segments.

3. An imaging detector according to claim 2 further including a high atomic number medium positioned between said segments for minimizing radiation crosstalk between said segments.

4. An imaging detector according to claim 3 wherein said high atomic number medium has a thickness less than 500 microns.

5. An imaging detector according to claim 1 wherein said scintillator segments are substantially comprised of CsI[Tl].

6. An imaging detector according to claim 1 further including a thermoelectric cooler for cooling said photodetector array.

7. An imaging detector according to claim 6 further including a substantially optically transparent thermal layer mounted between said scintillator and said photodetector array.

8. An imaging detector according to claim 7 wherein said thermal layer is a thermal insulator.

9. An imaging detector according to claim 7 wherein said thermal layer is thermal conductor.

10. An imaging detector according to claim 6 and further including an electronic circuit for rejecting Compton and other secondary radiation.

11. An imaging detector according to claim 6 and further including software for rejecting Compton and other secondary radiation.

12. An imaging detector according to claim 6 wherein said photodetector array comprises a plurality of P-I-N photodiodes.

13. An imaging detector according to claim 1 further including a substantially air-tight enclosure for containing said imaging detector wherein said enclosure is substantially filled with a dry gas.

14. The imaging detector of claim 1 further including:
   substantially low stray-capacitance couplings between the photodetector array elements and the readout electronics channels.

15. An imaging detector according to claim 1 further including a substantially air-tight enclosure filled with a dry gas and housing the collimator, scintillator, and photodetector therein.

16. An imaging detector for collimating and detecting individual x-ray or gamma ray photons, comprising:
   a collimator including a plurality of N×M chambers for controlling a direction of propagation of said photons;
   a scintillator comprising N×M segments for producing light in response to an interaction of said scintillator with said photons;
   a photodiode array including N×M elements disposed to receive said light and produce electrical signals in response thereto; and
   an array of N×M readout electronics channels coupled for communication with the respective elements for amplification and processing electrical signals produced by said photodiode array.

17. An imaging detector according to claim 16 further including a thermoelectric cooler for cooling said photodiode array.

18. An imaging detector according to claim 17 further including a substantially optically transparent thermal layer mounted between said scintillator and said photodiode array.

19. An imaging detector according to claim 18 wherein said thermal layer is a thermal insulator.

20. An imaging detector according to claim 16 wherein said scintillator is substantially comprised of CsI[Tl].

21. An imaging detector according to claim 16 further including substantially low stray capacitance couplings between the respective said elements and said channels.

22. An imaging detector according to claim 16 wherein said photodiode array comprises a plurality of P-I-N photodiodes.

23. A radiation imaging system for generating images by detecting scintillation radiation using a photodiode array, comprising:
  a radiation source for generating radiation;
  a collimator including a plurality of chambers for controlling a direction of propagation of said radiation;
  a scintillator for producing light in response to an interaction of said scintillator with said radiation;
  a photodiode array including a plurality of elements for producing electrical signals in response to said light;
  a substantially optically transparent thermal layer mounted between said scintillator and said photodiode array;
  a cooler for cooling said photodiode array; and
  a display device adapted to receive said electrical signals for generating an image for display.

24. A radiation imaging system according to claim 23 wherein said radiation source produces radiation at an energy level less than 200 keV.

25. A radiation imaging system according to claim 23 wherein said photodiode array comprises a plurality of P-I-N photodiodes.

26. A radiation imaging system according to claim 23 wherein said scintillator is substantially comprised of CsI[Tl].

27. An imaging detector for collimating and detecting radiation, comprising:
  a collimator including a plurality of chambers, each chamber having an end defining an exit aperture cross section;
  a scintillator including a plurality of segments, each segment having a first end defining a first aperture cross section aligned with a respective one of said exit aperture cross sections and having a second end defining a second aperture cross section;
  a photodetector array including a plurality of elements, each element having a cross section aligned with a respective one of said second aperture cross sections;
  a thermoelectric cooler for cooling said photodetector array; and
  a substantially optically transparent thermal layer mounted between said scintillator and said photodetector array.

28. An imaging detector according to claim 27 wherein said thermal layer is a thermal insulator.

29. An imaging detector according to claim 27 wherein said thermal layer is a thermal conductor.

30. An imaging detector for collimating and detecting radiation, comprising:
  a collimator including a plurality of chambers for controlling a direction of propagation of said radiation;
  a scintillator for producing light in response to an interaction of said scintillator with said radiation;
  a photodiode array including a plurality of elements disposed to receive said light and produce electrical signals in response thereto;
  a thermoelectric cooler for cooling said photodiode array; and
  a substantially optically transparent thermal layer mounted between said scintillator and said photodiode array.

31. An imaging detector according to claim 30 wherein said thermal layer is a thermal insulator.

32. An imaging detector according to claim 30 wherein said thermal layer is a thermal conductor.

* * * * *